United States Patent [19]

Rodewald

[11] 3,992,473

[45] *Nov. 16, 1976

[54] PARAFFIN ISOMERIZATION IN THE PRESENCE OF ISOBUTANE OR ISOPENTANE AND A CATALYST OF ALUMINUM CHLORIDE INTERCALATED IN GRAPHITE

[75] Inventor: Paul Gerhard Rodewald, Rocky Hill, N.J.

[73] Assignee: Mobil Oil Corporation, New York, N.Y.

[ * ] Notice: The portion of the term of this patent subsequent to Dec. 9, 1992, has been disclaimed.

[22] Filed: Apr. 4, 1975

[21] Appl. No.: 565,181

[52] U.S. Cl. ............................................ 260/683.7
[51] Int. Cl.$^2$............................................. C07C 5/28
[58] Field of Search........ 260/683.7, 683.65, 683.68

[56] References Cited

UNITED STATES PATENTS

| | | | |
|---|---|---|---|
| 2,425,268 | 8/1947 | Sensel | 260/683.68 |
| 3,394,202 | 7/1968 | Oelderik | 260/683.68 |
| 3,903,196 | 9/1975 | Kemp | 260/683.68 |
| 3,907,913 | 9/1975 | Kemp | 260/683.68 |
| 3,925,495 | 12/1975 | Rodewald | 260/683.68 |

*Primary Examiner*—George Crasanakis
*Attorney, Agent, or Firm*—Charles A. Huggett; Raymond W. Barclay

[57] ABSTRACT

Isomerization of normal paraffin hydrocarbons with 5 to 7 carbon atoms per molecule to isoparaffins of high octane number is effected in the presence of at least one compound of the group isobutane and isopentane and a catalyst consisting essentially of graphite having intercalated in the lattice thereof between about 5 and about 55 weight percent of aluminum chloride.

10 Claims, No Drawings

PARAFFIN ISOMERIZATION IN THE PRESENCE OF ISOBUTANE OR ISOPENTANE AND A CATALYST OF ALUMINUM CHLORIDE INTERCALATED IN GRAPHITE

BACKGROUND OF THE INVENTION

1. Field of the Invention

This invention relates to the isomerization of paraffin hydrocarbon with 5 to 7 carbon atoms per molecule in the presence of isobutane or isopentane and a catalyst of graphite having aluminum chloride intercalated therein.

2. Description of the Prior Art

A catalyst of aluminum chloride and platinum both intercalated in graphite has, as more particularly set forth in my copending application Ser. No. 467,316 filed May 6, 1974, which issued as U.S. Pat. No. 3,925,495 on Dec. 9, 1975, been found to be active for effecting low temperature isomerization of normal paraffins, e.g. n-hexane, in the presence of hydrogen. Initial activity of such catalyst is high but unfortunately of rather short life, decreasing, for example, from a conversion of approximately 80 to 90% to 10 to 20% after one day on stream.

SUMMARY OF THE INVENTION

In accordance with the present invention, it has been found that the addition of isobutane and/or isopentane to the n-paraffin feed significantly increases catalyst life during isomerization. In addition, the presence of platinum and hydrogen was found to be no longer required. The elimination of need for hydrogen recycle and platinum catalyst component markedly reduces the severity of pretreatment to remove sulfur from the feedstock. Moreover, substitution of isobutane and/or isopentane for platinum and hydrogen has economic advantages attributable to eliminating the cost of platinum and the expense of operating high pressure compressors.

There is thus provided, in accordance with the present invention, a process for isomerization of a feedstock consisting predominately of normal paraffin hydrocarbons containing 5 to 7 carbon atoms per molecule to isoparaffins of high octane number, e.g. dimethylbutanes, by contacting the same, in the presence of at least one compound of the group isobutane and isopentane, with a catalyst consisting essentially of graphite having intercalated in the lattice thereof between about 5 and about 55 weight percent of aluminum chloride.

The feedstock undergoing isomerization includes n-paraffins with 5 to 7 carbon atoms, i.e. pentane, hexane or heptane or mixtures thereof in which these n-paraffins predominate. Representative of suitable commercial mixtures are light naphtha fractions and straight-run tops which are generally available in large amounts in petroleum refineries. When utilizing these commercial mixtures as feedstocks, it is usually desirable to subject the same to a pretreatment to remove unwanted constituents such as unsaturated compounds, benzene, water and sulfur compounds. Although, as noted hereinabove, the severity of pretreatment to remove sulfur from the feedstock may, with the catalyst utilized in the present process, be substantially less than when the employed catalyst contains platinum.

The graphite utilized in the present catalyst is desirably characterized by a surface area of about 0.3 to about 50 m²/gram; a typical graphite applicable for use in the present invention is characterized by the following properties:

| | |
|---|---|
| Surface Area of | 0.46 m$^2$/gram |
| Real Density of | 2.16 gram/cc |
| Particle Density of | 1.90 gram/cc |
| Pore Volume of | 0.065 cc/gram |

Aluminum chloride is intercalated in the lattice of graphite in an amount generally between about 5 and about 55 weight percent. Intercalation is effected by heating a mixture of graphite and aluminum chloride, generally in the presence of chlorine, at a temperature between about 80° C. and about 150° C., preferably at approximately 110° C. for a period of between about 1 and about 72 hours.

In carrying out isomerization of the $C_5$ to $C_7$ normal paraffins utilizing the above-described catalyst, isobutane and/or isopentane in an amount of between about 5 and about 60 weight percent of the n-paraffin feedstock is introduced into the reaction zone. The isobutane and/or isopentane may be conducted to such zone as a separate stream or initially mixed with the n-paraffin feedstock being conducted to the reaction zone. Isobutane can be generated in situ in the reaction zone by the introduction into this zone of n-butane as such or in admixture with isobutane. Under the prevailing reaction conditions in such zone, n-butane is rapidly isomerized to isobutane. Likewise, isopentane can be generated in the reaction zone via introduction of n-pentane which undergoes rapid isomerization under the prevailing reaction conditions.

Contact between the catalyst, n-paraffin feedstock and isobutane and/or isopentane is conducted at a temperature between about 0° C. and about 200° C. and preferably between about 20° C. and about 150° C. at a pressure between about atmospheric and about 30 atmospheres or more. Low temperature isomerization of n-hexane, i.e. at 0° C. to 100° C., is particularly advantageous since the equilibrium concentration of high octane 2,2-dimethylbutane is high at low temperature. The catalyst to n-paraffin feedstock weight ratio employed is generally between about 1:5 and about 1:20. The hydrocarbons are passed over the catalyst at a liquid hourly space velocity generally between about 0.2 and about 10 and preferably between about 0.5 and about 4. The resulting product is withdrawn from the reaction zone, separated from the reactor effluent and recovered by any suitable means such as fractional distillation. Any unreacted starting material may be recycled to form a portion of the feedstock. Isobutane and/or isopentane which does not undergo reaction under the conditions for isomerization of the n-paraffin charge, is recoverable and may readily be recycled for further use.

Contact between the catalyst and n-paraffin feedstock may take place utilizing any of the conventional systems such as a fixed bed system, a moving bed system, a fluidized be system or a continuous or batch-type operation. Isomerization utilizing the present process may be carried out as either a vapor phase, a liquid phase or a mixed phase operation. Conversion may take place in the absence or presence of hydrogen. While operation in the presence of hydrogen can be of advantage for isomerization in preserving catalyst life, it is generally unnecessary, in accordance with the present process to utilize hydrogen since the presence of isobutane and/or isopentane in the reaction zone has been found to prolong life of the catalyst and thus eliminate the need for hydrogen.

DESCRIPTION OF SPECIFIC EMBODIMENTS

The following examples will serve to illustrate the process of this invention without limiting the same:

EXAMPLE 1

A 50 weight percent $AlCl_3$/graphite intercalate was prepared by heating 10 grams of $AlCl_3$ and 10 grams of graphite at 110° C. overnight in the presence of chlorine.

A reactor was packed with 4 cc of the above intercalate as catalyst and placed in a pressurized flow system. Dry n-hexane containing 40 percent by weight isobutane and 0.2 weight percent of t-butyl chloride was pumped upwardly at a liquid hourly space velocity of 1 through the catalyst bed maintained at 80° C.

The n-hexane conversion became constant at 80±5%. After three days on stream, the experiment was terminated. The following table shows the product composition exclusive of isobutane after three days on stream (76 n-hexane conversion):

| Component | Wt % |
|---|---|
| Propane | 0.1 |
| Butane | 1.4 |
| 2-Methylbutane | 24.2 |
| Pentane | 3.2 |
| 2-Methylpentane and 2,3-Dimethylbutane | 25.5 |
| 3-Methylpentane | 9.0 |
| 2,2-Dimethylbutane | 8.0 |
| Hexane | 24.5 |
| $C_7^+$ | 4.2 |

EXAMPLE 2

A reactor was packed with 4 cc of the catalyst described in Example 1 and placed in a pressurized flow system. Dry n-hexane containing 40 percent by weight isopentane and 0.2 percent by weight t-butyl chloride was pumped upwardly at a liquid hourly space velocity of 1 through the catalyst bed maintained at 80° C. The following table shows the product composition after three days on stream:

| Component | Wt % |
|---|---|
| Propane | 0.1 |
| 2-Methylpropane | 9.3 |
| Butane | 0.2 |
| 2-Methylbutane | 21.6 |
| Pentane | 1.3 |
| 2-Methylpentane and 2,3-Dimethylbutane | 11.2 |
| 3-Methylpentane | 3.9 |
| 2,2-Dimethylbutane | 0.3 |
| Hexane | 49.9 |

-continued

| Component | Wt % |
|---|---|
| $C_7^+$ | 2.2 |

It is to be understood that the foregoing description is merely illustrative of preferred embodiments of the invention of which many variations may be made by those skilled in the art within the scope of the following claims without departing from the spirit thereof.

I claim:
1. A process for effecting isomerization of a feedstock containing predominately normal paraffin hydrocarbons of 5 to 7 carbon atoms per molecule which comprises contacting said feedstock in a reaction zone, with between about 5 and about 60 weight percent of at least one compound selected from the group consisting of isobutane and isopentane and with a catalyst consisting essentially of graphite having intercalated in the lattice thereof between about 5 and about 55 weight percent of aluminum chloride, said reaction zone being maintained at a temperature between about 0° C. and about 200° C. and at a liquid hourly space velocity between about 0.2 and about 10 to yield a product containing isoparaffins of higher octane number than said normal paraffin hydrocarbons in said feedstock.

2. The process of claim 1 wherein said feedstock is n-hexane.

3. The process of claim 1 wherein said compound is isobutane.

4. The process of claim 1 wherein said compound is isopentane.

5. The process of claim 1 wherein said temperature is between about 20° C. and about 150° C. and said liquid hourly space velocity is between about 0.5 and about 4.

6. A process for effecting isomerization of a feedstock containing predominately normal paraffin hydrocarbons of 5 to 7 carbon atoms per molecule which comprises contacting said feedstock in a reaction zone, with between about 5 and about 60 weight percent of at least one compound selected from the group consisting of isobutane and isopentane and with a catalyst consisting essentially of graphite having intercalated in the lattice thereof between about 5 and about 55 weight percent of aluminum chloride, said reaction zone being maintained at a temperature between about 0° C. and about 200° C. and at a liquid hourly space velocity between about 0.2 and about 10 to yield a product containing isoparaffins of higher octane number than said normal paraffin hydrocarbons in said feedstock, separating said product from said at least one compound and recycling the latter to said reaction zone.

7. The process of claim 6 wherein said feedstock is n-hexane.

8. The process of claim 6 wherein said compound is isobutane.

9. The process of claim 6 wherein said compound is isopentane.

10. The process of claim 6 wherein said temperature is between about 20° C. and about 150° C. and said liquid hourly space velocity is between about 0.5 and about 4.

* * * * *